US010314981B2

United States Patent
Sampson et al.

(10) Patent No.: US 10,314,981 B2
(45) Date of Patent: Jun. 11, 2019

(54) THERMAL LOCKING MECHANISM FOR A MEDICATION DELIVERY DEVICE

(71) Applicant: Eli Lilly and Company, Indianapolis, IN (US)

(72) Inventors: Craig Field Sampson, Lake Bluff, IL (US); Jacob S. Brauer, Cambridge, MA (US); Stuart Desha Breslin, Danville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 14 days.

(21) Appl. No.: 15/518,559

(22) PCT Filed: Nov. 11, 2015

(86) PCT No.: PCT/US2015/060118
§ 371 (c)(1),
(2) Date: Apr. 12, 2017

(87) PCT Pub. No.: WO2016/081238
PCT Pub. Date: May 26, 2016

(65) Prior Publication Data
US 2017/0224929 A1    Aug. 10, 2017

Related U.S. Application Data

(60) Provisional application No. 62/081,244, filed on Nov. 18, 2014.

(51) Int. Cl.
*A61M 5/20* (2006.01)
*A61M 5/24* (2006.01)
*A61M 5/315* (2006.01)

(52) U.S. Cl.
CPC .......... *A61M 5/31571* (2013.01); *A61M 5/20* (2013.01); *A61M 5/24* (2013.01);
(Continued)

(58) Field of Classification Search
CPC ....... A61M 5/31571; A61M 5/20; A61M 5/24
See application file for complete search history.

(56) References Cited

U.S. PATENT DOCUMENTS

| 5,170,779 A | 12/1992 | Ginsberg |
| 5,738,658 A | 4/1998 | Maus et al. |

(Continued)

FOREIGN PATENT DOCUMENTS

| EP | 2087917 | 8/2009 |
| GB | 2490721 | 11/2012 |

(Continued)

OTHER PUBLICATIONS

Patent Cooperation Treaty International Search Report and Written Opinion of the International Searching Authority pertaining to International Application No. PCT/US2015/060118; dated Feb. 4, 2016.

*Primary Examiner* — Edelmira Bosques
(74) *Attorney, Agent, or Firm* — Daniel Spillman

(57) ABSTRACT

A medication injection device (2) includes a housing (4) and a needled syringe (8) supported by the housing. The needle syringe has a plunger (10) and a volume containing medication. The medication injection device further includes an expelling mechanism (6) operably coupled to the plunger. Additionally, the device includes a thermal locking mechanism (20) operably coupled to the expelling mechanism, comprising a material which is solid when the device is refrigerated and transitions to a liquid or gel-like state at a phase-change temperature when the device is taken out of refrigeration and warms up together with the contained drug to a temperature which is suitable for performing an injection. In the solid state, the material keeps the expelling mechanism locked in a disabling condition inhibiting delivery of the medication and in its liquid state creates an enabling condition permitting delivery of the medication.

21 Claims, 9 Drawing Sheets

(52) U.S. Cl.
CPC ......... *A61M 2005/206* (2013.01); *A61M 2005/2073* (2013.01); *A61M 2205/276* (2013.01); *A61M 2205/3368* (2013.01)

(56) References Cited

U.S. PATENT DOCUMENTS

| | | | |
|---|---|---|---|
| 7,566,326 | B2 | 7/2009 | Duchon et al. |
| 7,762,981 | B2 | 7/2010 | Dacquay et al. |
| 8,133,198 | B2 * | 3/2012 | Neer .......... A61M 5/145 604/131 |
| 2007/0270777 | A1 | 11/2007 | Dacquay et al. |
| 2008/0097390 | A1 | 4/2008 | Dacquay et al. |
| 2009/0036868 | A1 | 2/2009 | Pinedjian et al. |

FOREIGN PATENT DOCUMENTS

| | | |
|---|---|---|
| WO | 9817332 | 4/1998 |
| WO | 0137906 | 5/2001 |
| WO | 0147586 | 7/2001 |
| WO | 02/28458 | 4/2002 |
| WO | 03039635 | 5/2003 |
| WO | 2005072794 | 8/2005 |
| WO | 2009022132 | 2/2009 |
| WO | 2011091246 | 7/2011 |
| WO | 2012153150 | 11/2012 |
| WO | 2014099831 | 6/2014 |

* cited by examiner

FIG_4

FIG_6

THERMAL LOCKING MECHANISM FOR A MEDICATION DELIVERY DEVICE

FIELD OF THE DISCLOSURE

The present disclosure relates generally to a locking mechanism for a medication delivery device and, more particularly, to a thermal locking mechanism for a medication injection device.

BACKGROUND OF THE DISCLOSURE

Patients suffering from a number of different diseases frequently must inject themselves with pharmaceuticals or other medications. A variety of devices have been proposed to facilitate these injections. One type of device is an injection device, which may be either a manual, or non-automatic, injection device or an automatic injection device.

Some injection devices and medication are stored at low temperatures (e.g., in a refrigerator). At such temperatures the medication may be more viscous than at room temperature. Therefore, if used in this refrigerated condition, the flow of medication through the needle and into the patient may be affected. For example, the increased viscosity of the medication may require the user to apply more force to the injection device to fully administer the medication. Furthermore, the increased viscosity of the medication may result in an incomplete injection because a portion of the medication was not dispensed from the injection device within a given amount of time. Additionally, the injection of medication may be less comfortable for the recipient when the medication is at lower temperatures than when the temperature of the medication has increased. Therefore it is preferred that the device and medication be close to room temperature when used. For example, some injection devices may specify that the user should remove the injection device and medication from the refrigerator and wait 15-30 minutes before administering the medication from the injection device to allow the temperature of the medication to increase and the viscosity of the medication to decrease. However, the injection device may still be used at the decreased temperatures if the user did not want to wait, or is unaware of the instructions to wait.

Some injection devices may prevent the user from administering the medication from the injection device when the temperature of the device and/or medication is less than a predetermined temperature.

By removing the injection device and medication from the refrigerator, and delaying the administration of the medication, the temperature of the medication will increase and the viscosity will decrease which may allow the usage of the injection device to be faster, more comfortable for the patient and/or accurate or efficient.

SUMMARY OF THE DISCLOSURE

An exemplary embodiment of the present disclosure includes a medication delivery device having a housing and a needled syringe supported by the housing. The needled syringe includes a plunger and a volume configured to contain a medication. The medication delivery device also includes an expelling mechanism operably coupled to the plunger. The medication delivery device further includes a thermal locking member operably coupled to the expelling mechanism. The thermal locking mechanism has a phase-change temperature, and the thermal locking member has a disabling condition inhibiting delivery of the medication and an enabling condition permitting delivery of the medication. The locking member transitions between the disabling and enabling conditions at the phase-change temperature.

Another exemplary embodiment of the present disclosure includes a medication delivery device having a housing and a needled syringe supported by the housing. The needled syringe includes a plunger and a volume configured to contain a medication. The medication delivery device further includes an expelling mechanism operably coupled to the plunger and a thermal locking member supported by the housing. The thermal locking member has a disabling condition inhibiting delivery of the medication and an enabling condition permitting delivery of the medication. Additionally, the locking member has a solid phase when in the disabling condition and a liquid phase when in the enabling condition.

A further exemplary embodiment of the present disclosure includes a medication delivery device having means for housing a medication, means for delivering the medication, and means for triggering actuation of the delivering means. Additionally, the medication delivery device includes a thermal locking member supported by the housing means and operably coupled to at least one of the delivering means and the triggering means. The thermal locking member has a phase-change temperature and is configured to change physical phases at the phase-change temperature.

Additional features and advantages of the present invention will become apparent to those skilled in the art upon consideration of the following detailed description of the illustrative embodiment exemplifying the best mode of carrying out the disclosure as presently perceived.

BRIEF DESCRIPTION OF THE DRAWINGS

The foregoing aspects and many of the intended advantages of this disclosure will become more readily appreciated as the same becomes better understood by reference to the following detailed description when taken in conjunction with the accompanying drawings.

Figure 1:
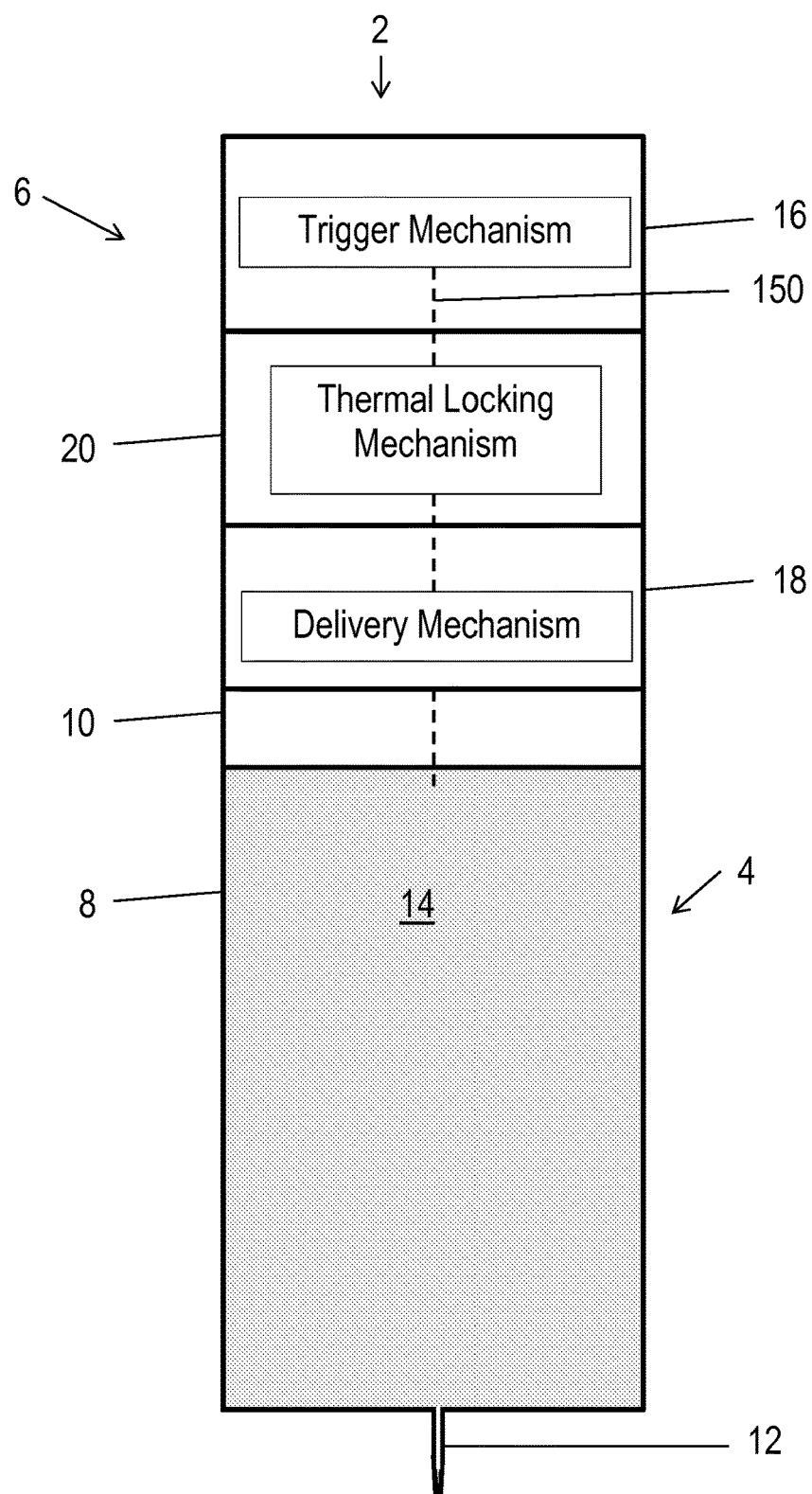
FIG. 1 is a schematic view of a medication delivery device of the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the invention, and such exemplifications are not to be construed as limiting the scope of the invention in any manner.

DETAILED DESCRIPTION OF THE DRAWINGS

For the purposes of promoting an understanding of the principals of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrative devices and described methods and further applications of the principles of the invention which would normally occur to one skilled in the art to which the invention relates.

Referring to FIG. 1, a medication delivery device 2 of the present disclosure is illustratively shown as an automatic injection device. However, medication delivery device 2 also may be a self- or non-automatic injection device or other device configured to administer medication to a patient. Medication delivery device 2 includes a housing 4, an expelling mechanism 6, and a syringe 8. Housing 4 supports syringe 8 which includes a piston 10, a needle 12, and a volume for containing a medication 14. During injection of a dosage of medication 14 into a patient, piston 10 moves toward needle 12 and the dosage of medication 14 flows through needle 12.

Housing 4 is operably coupled to expelling mechanism 6, which includes a trigger mechanism 16 and a delivery mechanism 18. As shown by dashes 150, trigger mechanism 16 is operably coupled to delivery mechanism 18 to initiate administration of a dosage of medication 14 to a patient. More particularly, a user may actuate trigger mechanism 16 which actuates delivery mechanism 18 to act on piston 10 and administer a dosage of medication 14 to the patient through needle 12.

Medication delivery device 2 also includes a thermally-activated locking mechanism 20 operably coupled to trigger mechanism 16 and housing 4. Locking mechanism 20 is positioned intermediate trigger mechanism 16 and housing 4. Locking mechanism 20 may enable use of medication delivery device 2 or disable use of medication delivery device 2 at predetermined temperatures. For example, locking mechanism 20 may be a phase-change material having a phase-change temperature at which locking mechanism 20 changes or transitions between phases or conditions. More particularly, at the phase-change temperature, locking mechanism 20 is configured to change between a first (solid) phase disabling operation of expelling mechanism 6 and a second (liquid) phase enabling operation of expelling mechanism 6.

The exemplary embodiment of locking mechanism 20 is configured to change from a solid phase to a liquid phase, at the phase-change temperature. When locking mechanism 20 is in the solid phase, locking mechanism 20 is in a disabling condition such that locking mechanism 20 inhibits, blocks, or otherwise prevents actuation of medication delivery device 2 and medication 14 cannot be administered to a patient. More particularly, when locking mechanism 20 is in the solid phase, locking mechanism 20 inhibits actuation of trigger mechanism 16, which thereby inhibits actuation of delivery mechanism 18. However, when locking mechanism 20 is in the liquid phase, locking mechanism 20 is in the enabling condition such that locking mechanism 20 permits or allows actuation of medication delivery device 2 and medication 14 may be administered to the patient through needle 12. More particularly, when locking mechanism 20 is in the liquid phase, locking mechanism permits actuation of trigger mechanism 16, which thereby permits actuation of delivery mechanism 18 and allows medication 14 to flow through needle 12.

Figure 2:
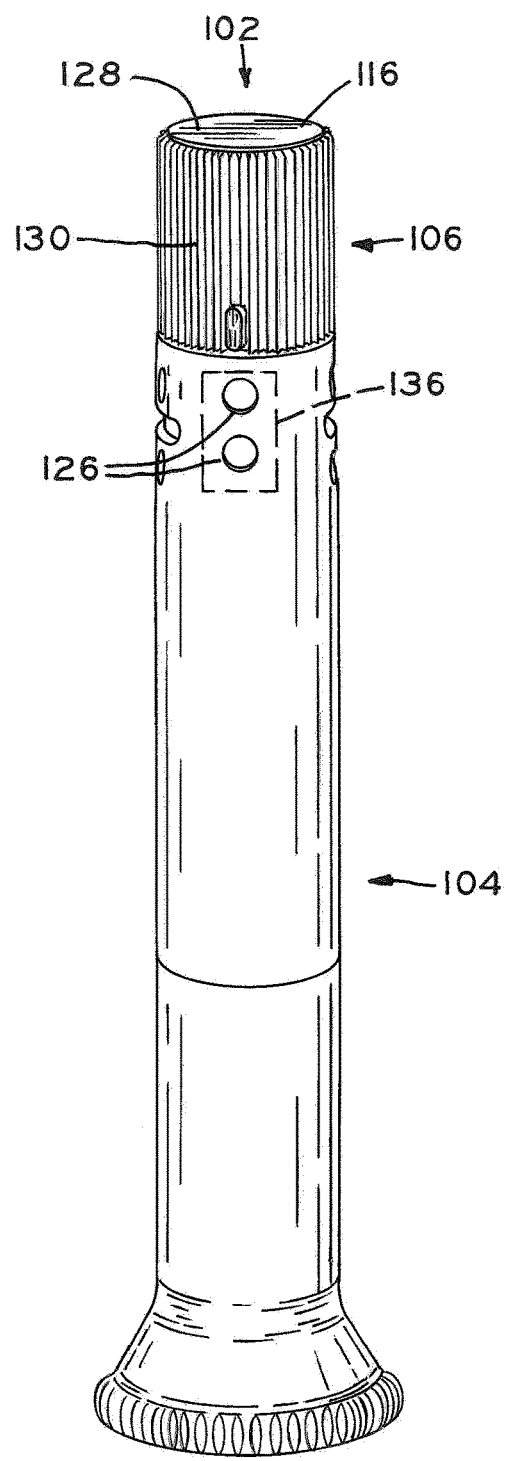
FIG. 2 is a front perspective view of a preferred embodiment of a medication delivery device, showing circular injection ports for a thermal locking mechanism that controls delivery of the medication.

Referring to FIG. 2, a preferred medication delivery device 102 is shown as an automatic injection device. However, medication delivery device 102 also may be configured as a self- or non-automatic injection device. Medication delivery device 102 includes a housing 104, an expelling mechanism 106, and a syringe 108 (see FIG. 3). Additionally, medication delivery device 102 includes a preferred embodiment thermal locking mechanism 120 (see FIG. 7). Housing 104 may be comprised of a polymeric material, for example acrylonitrile butadiene styrene ("ABS"), or any other material suitable for medication delivery devices. Illustratively, housing 104 is generally cylindrically-shaped and extends longitudinally; however, housing 104 may be provided in other configurations. Additionally, in one embodiment, housing 104 is comprised of a single housing member extending longitudinally. Alternatively, housing 104 may be a housing assembly comprised of a plurality of housing members coupled together.

Figure 4:
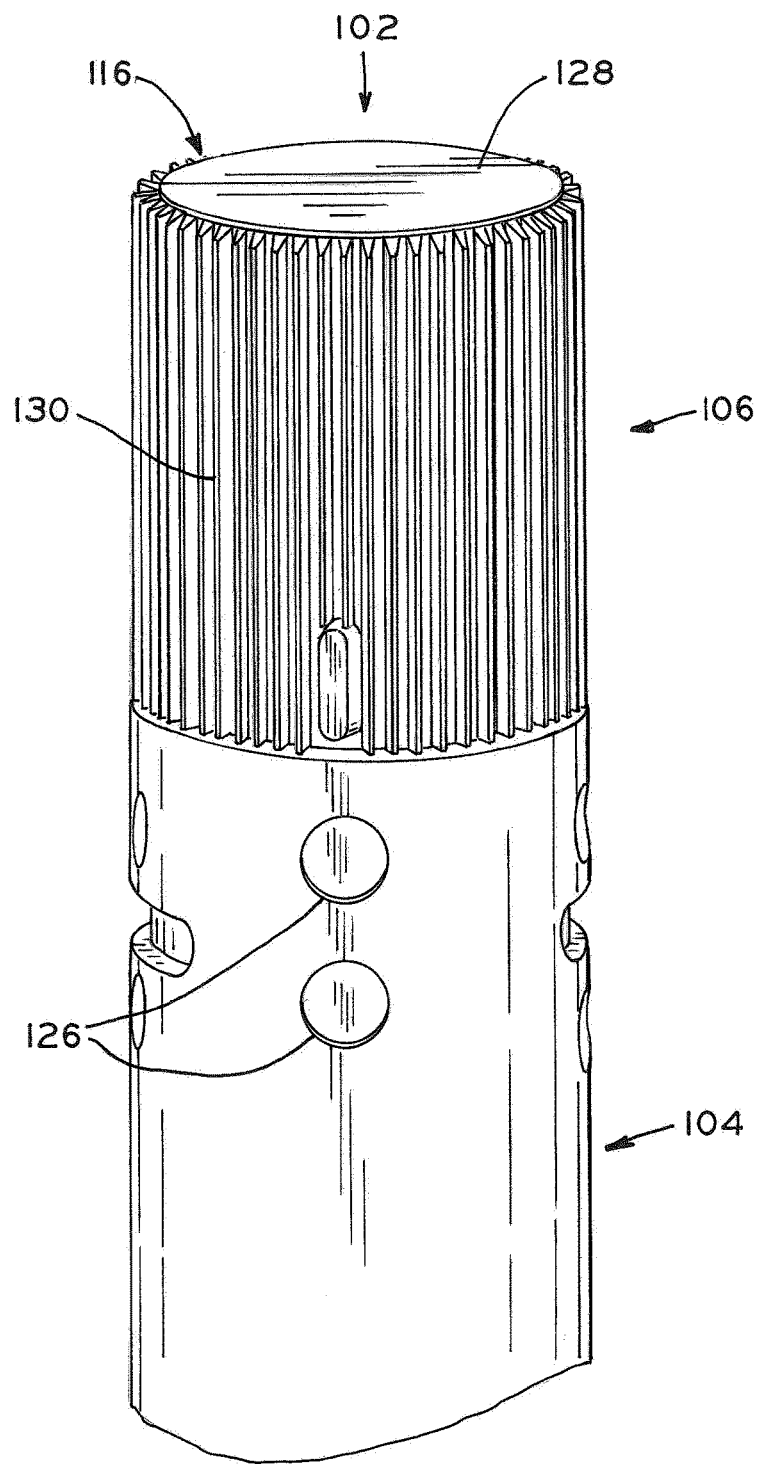
FIG. 4 is a front perspective view of an upper end of the medication delivery device of FIG. 2 showing the injection ports.
Figure 5:
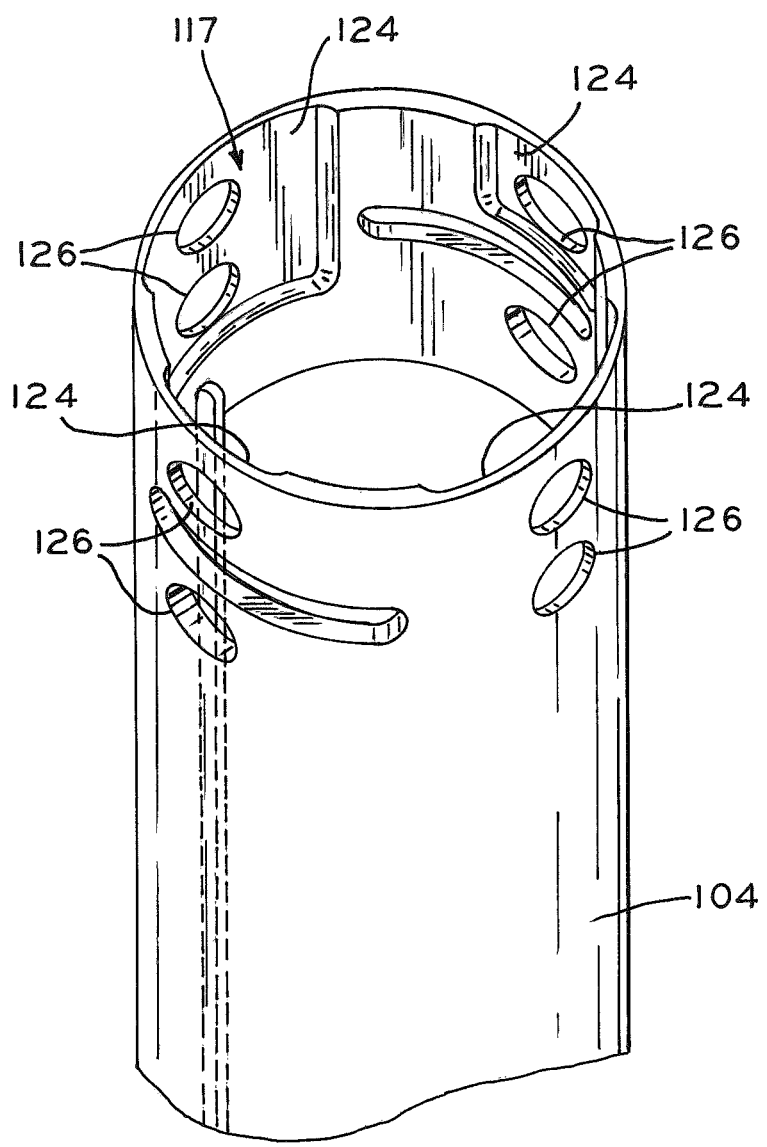
FIG. 5 is a top perspective view of a housing of the medication delivery device of FIG. 2 showing interior recesses that receive the thermal locking mechanism.

Housing 104 includes at least one recess 124 as shown in FIG. 5. Additionally, as shown in FIGS. 2, 4, and 5, housing 104 also may include at least one port or opening 126. Referring to FIG. 5, at least port 126 extends into each recess 124. In this way, and as detailed further herein, when locking mechanism 120 is in liquid form, it may be injected into recesses 124 through ports 126 during a manufacturing injection process and then covered to prevent the liquid from flowing out of ports 126.

Figure 3:
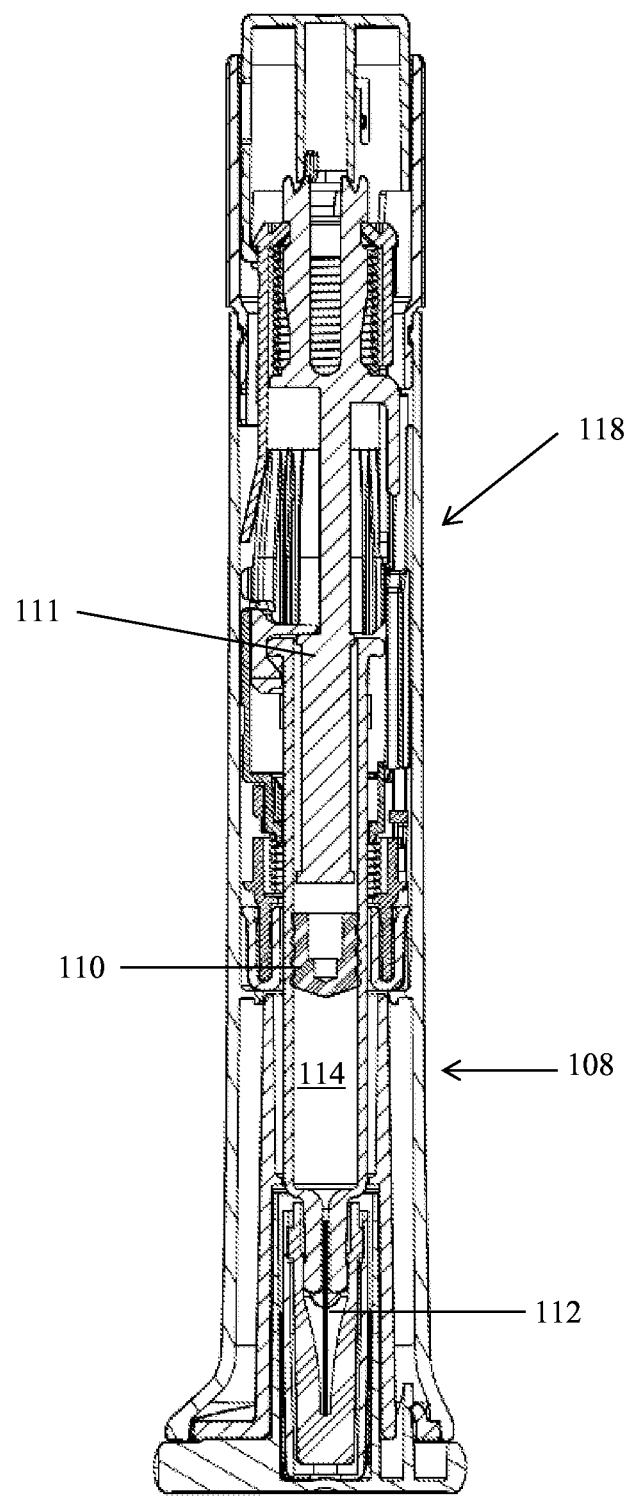
FIG. 3 is a cross-sectional view of preferred inner workings of the medication delivery device of FIG. 2.

Housing 104 supports syringe 108 at a lower end thereof. The preferred inner workings of syringe 108 are shown in FIG. 3. Syringe 108 includes a piston 110, a needle 112, and a volume containing medication 114. Needle 112 is in fluid communication with medication. The advancement of piston 110 by the movement of plunger 111 of delivery mechanism 116 causes medication 114 to flow through needle 112 during an injection. More particularly, when a dosage of medication 114 is injected into a patient, piston 110 moves toward needle 112 and the dosage of medication 114 flows through needle 112. Additional details of components of medication delivery device 102 not shown or described herein are provided in International Application No. PCT/US2011/025988, filed on Feb. 24, 2011, and published as International Publication No. WO 2011/109205 on Sep. 9, 2011, the complete disclosure of which is expressly incorporated by reference herein.

Housing 104 is operably coupled to expelling mechanism 106. As shown in FIGS. 2, 4, 6, and 8, expelling mechanism 106 of exemplary medication delivery device 102 is operably coupled to the upper end of housing 104. Components of expelling mechanism 106 may be comprised of a polymeric material, for example ABS, and also may be generally shaped as a cylinder. More particularly, components of expelling mechanism 106 may have a shape complementary to that of housing 4 and, illustratively, be configured to be received within the upper end of housing 104, as shown in FIG. 7.

Exemplary expelling mechanism 106 includes a trigger mechanism 116 and a delivery mechanism 118. Trigger mechanism 116 is operably coupled to delivery mechanism 118 to initiate the administration of a dosage of medication 114 to a patient. More particularly, a user may actuate trigger mechanism 116 which actuates delivery mechanism 118 to act on piston 110 to administer a dosage of medication 114 to the patient through needle 112.

Illustrative trigger mechanism 116 is operably coupled to delivery mechanism 118 and may be any mechanism configured to be actuated by a user to initiate an injection. For example, trigger mechanism 16 may include a first component, such as a trigger member or a button 128, configured to be actuated by a user to initiate the flow of medication 14 through needle 112 and into a patient, as detailed further herein. As described in greater detail below, thermal locking mechanism 120 blocks operation of trigger mechanism 116 to prevent initiation of the injection.

Because medication delivery device 102 is an automatic injection device, trigger mechanism 116 is included thereon. However, for self- or non-automatic embodiments of medication delivery device 102, trigger mechanism 116 may be modified or omitted. Additionally, for a self- or non-automatic medication delivery device, rather than blocking a trigger mechanism, a thermal locking mechanism may block other movement of the delivery mechanism. For example, the thermal locking mechanism may create interference with plunger depending upon the temperature of the thermal locking mechanism. Additional details related to a self- or non-automatic embodiment of medication delivery device 102 may be further shown and described in U.S. Pat. No. 6,454,746, issued on Sep. 24, 2002, the complete disclosure of which is expressly incorporated by reference herein.

Trigger mechanism 116 also may include a lock 130 generally surrounding button 128. Lock 130 is configured to be manually rotatable relative to housing 104 prior to initiating an injection with button 128. Lock 130 functions as a mechanical lock for medication delivery device 102 because button 128 cannot be depressed without first rotating lock 130. As such, failure to rotate lock 130 prevents a user from accidentally dispensing medication 114 from medication delivery device 102 if button 128 is inadvertently pressed.

Figure 6:
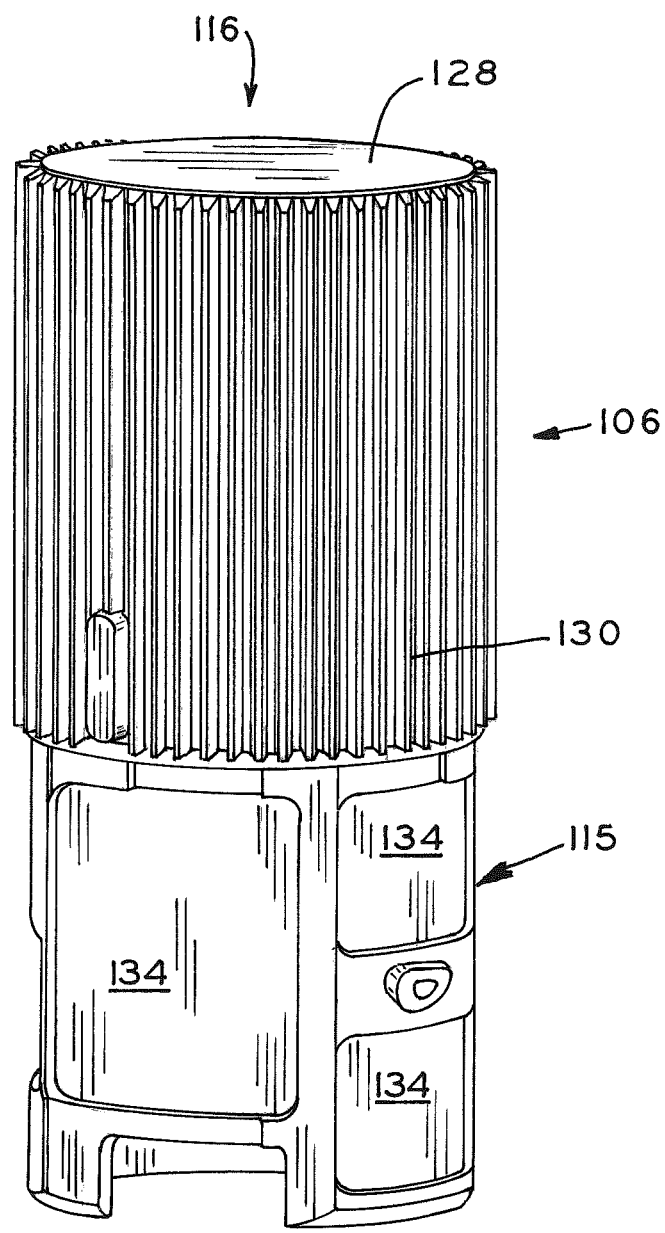
FIG. 6 is a perspective view of a portion of an expelling mechanism of the medication delivery device of FIG. 2 showing exterior recesses that receive the thermal locking mechanism.
Figure 7:
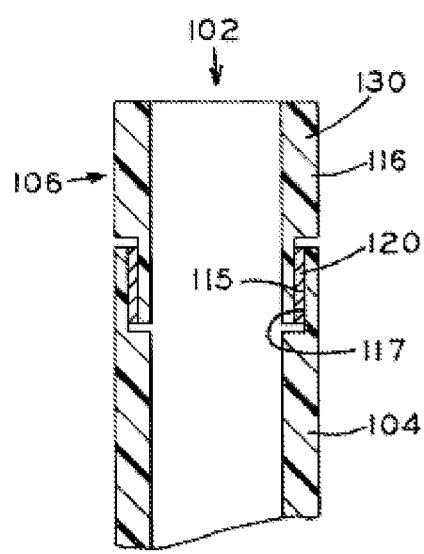
FIG. 7 is a schematic cross-sectional view of portions of the upper end of the medication delivery device of FIG. 2 with other portions omitted for clarity.

Lock 130 of trigger mechanism 116 may further include at least one recess 134, which may be defined along a lower portion of an outer surface 115 of lock 130, as shown in FIG. 6. Recesses 134 align with recesses 124 of housing 104 to define a volume or gap between outer surface 115 of lock 130 of trigger mechanism 116 and inner surface 117 of housing 104. As detailed further herein, locking mechanism 120 is received within this volume defined between housing 104 and trigger mechanism 116 when locking mechanism 120 is in a liquid phase.

Referring to FIG. 7, locking mechanism 120 is operably coupled to lock 130 of trigger mechanism 116 and housing 104. Locking mechanism 120 is positioned intermediate a lower end of lock 130 of trigger mechanism 116 and an upper end of housing 104. Locking mechanism 120 is a thermally-activated mechanism. In particular, locking mechanism 120 may enable or disable medication delivery device 102 at predetermined temperatures. For example, locking mechanism 120 may be a phase-change material having a phase-change temperature at which locking mechanism 120 changes or transitions between phases or conditions. More particularly, at the phase-change temperature, locking mechanism 120 is configured to change between a first (solid) phase and a second (liquid) phase when the area or space around locking mechanism 120 is warmer than the phase change temperature of locking mechanism 120.

The exemplary embodiment of locking mechanism 120 is configured to change from a solid phase to a liquid phase, at the phase-change temperature. When locking mechanism 120 is in the solid phase, locking mechanism 120 is in a disabling condition such that locking mechanism 120 inhibits, blocks, or otherwise prevents actuation of medication delivery device 102 and medication 114 cannot be administered to a patient. More particularly, when locking mechanism 120 is in the solid phase, locking mechanism 120 inhibits rotation of lock 130 of trigger mechanism 116, which thereby inhibits depression of button 128 and actuation of delivery mechanism 118. However, when locking mechanism 120 is in the liquid phase, locking mechanism 120 is in the enabling condition such that locking mechanism 120 permits or allows rotation of lock 130 and actuation of medication delivery device 102 and medication 114 may be administered to the patient through needle 112. More particularly, when locking mechanism 120 is in the liquid phase, locking mechanism 120 permits actuation of trigger mechanism 116 by allowing lock 130 to rotate to the unlocked position, which thereby permits actuation of delivery mechanism 118 and allows medication 114 to flow through needle 112.

As shown in FIG. 7, locking mechanism 120 is positioned intermediate lock 130 of trigger mechanism 116 and housing 104. More particularly, locking mechanism 120 is positioned along inner surface 117 of housing 104 and lower outer surface 115 of lock 130 of trigger mechanism 116. Illustratively, as shown in FIG. 5, locking mechanism 120 is received within the volume between housing 104 and lock 130 of trigger mechanism 116. In one embodiment, locking mechanism 120 has a shape that is generally the same as the shape of the volume defined by recesses 124, 134.

Figure 12:
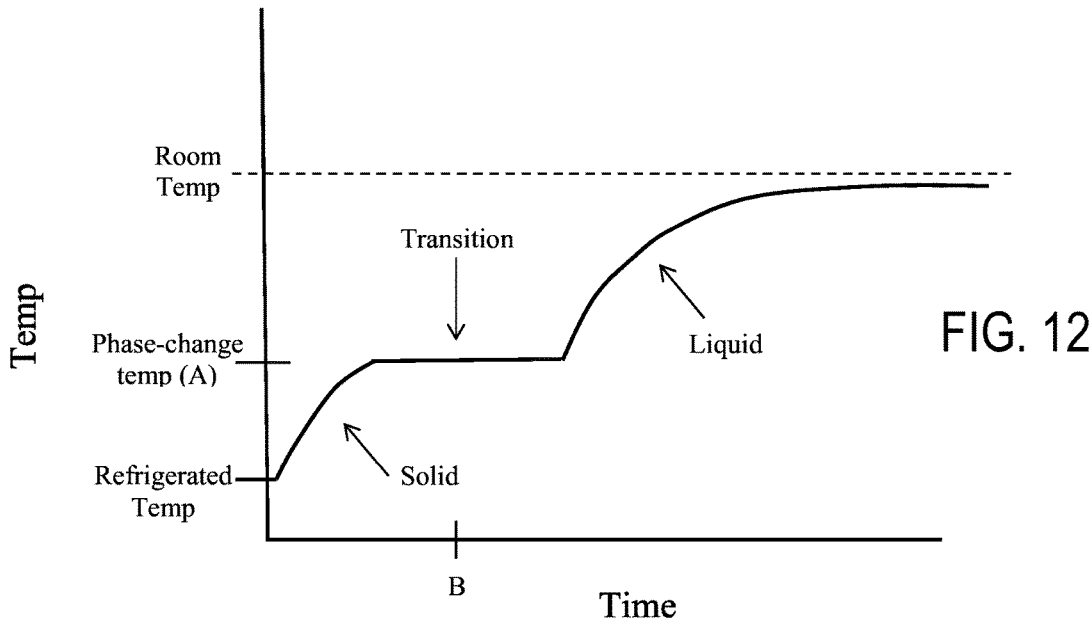
FIG. 12 is a graphical representation of the operation of the thermal locking mechanism of the medication delivery device of FIG. 2.

Referring to FIG. 12, when the temperature of locking mechanism 120 of medication delivery device 102 is below the phase-change temperature, denoted as A, locking mechanism 120 remains in the solid phase. However, when the temperature of locking mechanism 120 is at phase-change temperature A, for example at a time B, locking mechanism 120 will absorb thermal energy from the warmer environment to change phases and transition to the liquid phase when enough thermal energy is absorbed. During the transition between the solid phase and the liquid phase, the temperature of locking mechanism 120 does not increase because locking mechanism 120 is absorbing thermal energy to effectuate the phase change. As such, before time B, the temperature of locking mechanism 120 is below phase-change temperature A and locking mechanism 120 remains in the first or solid phase blocking rotation of lock 130. However, after time B, the temperature of locking mechanism 120 is at phase-change temperature A and locking mechanism 120 transitions to the second or liquid phase as it absorbs thermal energy permitting rotation of lock 130. After locking mechanism 120 absorbs enough thermal energy to completely change phase, its temperature will continue to rise toward the room temperature as shown in FIG. 12.

As detailed further herein, when locking mechanism 120 is at or above phase-change temperature A, locking mechanism 120 is in the liquid phase and lock 130 of trigger mechanism 116 of expelling mechanism 106 is configured to be rotatable relative to housing 104, thereby allowing the user to initiate the injection of medication 114. According to an alternative embodiment, when locking mechanism 120 is at or above phase-change temperature A and is in the liquid phase, lock 130 may be configured to pivot, slide, or otherwise move relative to housing 104 to allow the user to initiate the injection of medication 114.

When the temperature of locking mechanism 120 is above phase-change temperature A, locking mechanism 120 remains in the liquid phase. However, if the temperature of locking mechanism 120 decreases to phase-change temperature A, locking mechanism 120 will transition back to the solid phase as it loses thermal energy to the colder environment. In particular, as the temperature of locking mechanism 120 decreases to phase-change temperature A, locking mechanism 120 will lose thermal energy to effectuate the change from the liquid phase to the solid phase. During the transition from the liquid phase to the solid phase, the temperature of locking mechanism 120 does not decrease, but rather, remains constant at phase-change temperature A while locking mechanism 120 loses thermal energy and completely transitions back to the solid phase. After locking mechanism 120 has completed the transition to the solid phase, the temperature of locking mechanism 120 may decrease below phase-change temperature A. As detailed further herein, when locking mechanism 120 transitions from the liquid phase to the solid phase, lock 130 of expelling mechanism 106 is prevented from rotating, thereby preventing the user from administering medication 14.

Because locking mechanism 120 has one phase-change temperature A, locking mechanism 120 is configured to change between the solid phase and the liquid phase only at phase-change temperature A. More particularly, locking mechanism 120 changes or transitions from the solid phase to the liquid phase when the temperature of locking mechanism 120 increases to approximately phase-change temperature A and locking mechanism 120 absorbs thermal energy from the warmer environment. Additionally, locking mechanism 120 changes or transitions from the liquid phase to the solid phase when the temperature of locking mechanism 120 decreases to approximately phase-change temperature A. As such, the transitions between phases of locking mechanism 120 are not unidirectional, but instead, are bidirectional and allow locking mechanism 120 to change back and forth between the solid phase and the liquid phase whenever the temperature of locking mechanism 120 increases or decreases to phase-change temperature A and locking mechanism gains or loses sufficient thermal energy. In this way, the phase changes of locking mechanism 120 are reversible.

Furthermore, because locking mechanism 120 has only one phase-change temperature A, locking mechanism 120 has minimal or no hysteresis, such that the temperature at which locking mechanism 120 transitions from the solid phase to the liquid phase is approximately the same as the temperature at which locking mechanism 120 transitions from the liquid phase to the solid phase. For example, the hysteresis of locking mechanism 120 may be less than approximately 0.5° C. Without hysteresis, locking mechanism 120 may be used multiple times to enable and disable medication delivery device 102. As such, locking mechanism 120 can be used in a medication delivery device for multiple dosages of medication and multiple uses, as detailed further herein. Or, if locking mechanism 120 of medication delivery device 102 is heated above the phase change temperature without an injection taking place and then cooled below the phase change temperature, medical delivery device 102 can still be used because locking mechanism 120 is reversible.

In one embodiment, locking mechanism 120 is comprised of a paraffin wax material configured to change phases at a temperature of approximately 5-25° C., and more particularly, 14-20° C. In one embodiment, phase-change temperature A of locking mechanism 120 is approximately 17° C. Locking mechanism 120 also may be comprised of other materials with phase-change temperatures of approximately 5-25° C. As such, if medication delivery device 102 is stored in refrigerated or low-temperature conditions prior to use and then the temperature of locking mechanism 120 of medication delivery device 102 increases to approximately 17° C., exemplary locking mechanism 120 transitions from the solid phase to the liquid phase.

Figure 8:
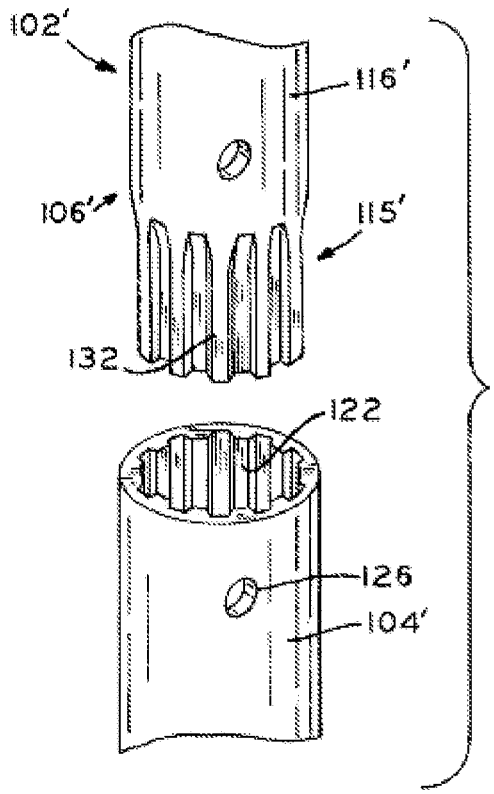
FIG. 8 is an exploded view of an alternative embodiment housing and an alternative embodiment portion of an expelling mechanism of a medication delivery device, showing alternative recesses for receiving a locking mechanism.

As shown in FIG. 8, an alternative embodiment medication delivery device 102' includes an upper end of housing 104' with a ribbed, knurled, gritted, grooved, recessed, or otherwise textured inner surface 122. As shown in FIG. 8, a lower portion of an outer surface 115' of trigger mechanism 116' may include a ribbed, knurled, gritted, grooved, recessed, or otherwise textured surface 132 configured to be received within textured surface 122 of housing 104'. More particularly, textured surface 122 is generally complementary to textured surface 132 and may facilitate the coupling between trigger mechanism 116' and housing 104' with locking mechanism 120. For example, textured surfaces 122, 132 may increase structural resistance of locking mechanism 120 against movement of expelling mechanism 106' relative to housing 104' when locking mechanism 120 is in the solid phase. During partial melting of locking mechanism 120, solid portions of locking mechanism 120 positioned in textured surfaces 122, 132 tend to prevent rotation of trigger mechanism 116' relative to upper end of housing 104' even though other portions of locking mechanism 120 are in a liquid phase. As such, more complete melting of locking mechanism 120 is required to enable medication delivery device 102'.

Medication delivery device 102 may further include an indicator 136 (shown in phantom) operably coupled to locking mechanism 120, as shown in FIG. 2. Indicator 136 indicates when locking mechanism 120 is at or above phase-change temperature A. For example, indicator 136 may include at least one symbol, such as a lock, words, and/or a color-coded portion, to indicate that locking mechanism 120 is at or above phase-change temperature A. In one embodiment, indicator 136 may be a printed leuco-dye label operably coupled to locking mechanism 120. More particularly, as shown in FIG. 2, indicator 36 may be adhered or otherwise coupled to housing 104 and in at least thermal contact with locking mechanism 120. For example, indicator 136 may be coupled to housing 104 over injection ports 126 such that indicator 136 is adjacent locking mechanism 120 via injection ports 126. In another embodiment, indicator 136 may be a dye mixed locking mechanism 120 that is visible though a transparent portion of housing 104.

During manufacture and assembly of medication delivery device 102, expelling mechanism 106 is received within housing 104 such that recesses 124, 134 align with each other. Locking mechanism 120 is injected through ports 126 into the volume defined between recesses 124, 134 while locking mechanism 120 is in the liquid phase. In this way, locking mechanism 120 is initially received within the volume defined by recesses 124, 134 in the liquid phase and then transitions to the solid phase as the temperature of locking mechanism 120 decreases. As such, locking mechanism 120 generally takes the shape of the volume defined by recesses 124, 134 and fills the void or gap between housing 104 and expelling mechanism 106, as shown in FIG. 7. When in the solid phase, locking mechanism 120 is a solid mass with high shear strength which completely fills the volume between housing 104 and trigger mechanism 116 such that there is minimal or no tolerance between housing 104 and trigger mechanism 116.

After assembly, medication delivery device 102 is used to inject a dosage of medication 114 into a patient. Prior to use of medication delivery device 102, the user may store medication delivery device 102 in a refrigerated or low-temperature condition. When at the decreased temperature, the viscosity of medication 114 may increase such that administering medication 114 from medication delivery device 102 at the decreased temperature may be less comfortable for the recipient or result in an incomplete dosage. As such, exemplary medication delivery device 102 is configured to prevent the user from administering medication 114 until the temperature of medication delivery device 102 has increased to a predetermined temperature.

More particularly, when locking mechanism 120 of medication delivery device 102 is at a temperature below phase-change temperature A, locking mechanism 120 is in the solid phase. In this way, locking mechanism 120 is in the disabling condition and the user is unable to actuate expelling mechanism 106 to administer medication 114 because locking mechanism 120 prevents lock 130 of trigger mechanism 116 from rotating relative to housing 104. Button 128 of trigger mechanism 116 cannot be actuated unless lock 130 moves and, therefore, because lock 130 cannot move when locking mechanism 120 is in the solid phase, button 128 cannot be depressed to initiate actuation of delivery mechanism 118.

After medication delivery device 102 is removed from the refrigerated or low-temperature condition, the user will wait until the temperature of locking mechanism 120 increases to at least phase-change temperature A before administering medication 114. The temperature of locking mechanism 120 is configured to increase at substantially the same rate at which the temperature of medication 114 increases, such that when the temperature of locking mechanism 120 increases to phase-change temperature A, the temperature of medication 114 also increases to the desired temperature for administering to the patient. As such, the phase-change temperature A of locking mechanism 120 corresponds to the preferred predetermined temperature at which medication 114 should be used. When the temperature of locking mechanism 120 increases to phase-change temperature A at time B (see FIG. 12), the temperature of medication 114 also increases to the preferred predetermined temperature at time B.

When the temperature of locking mechanism 120 increases to at least phase-change temperature A, locking mechanism 120 transitions from the solid phase to the liquid phase as it absorbs thermal energy. As such, locking mechanism 120 transitions from the disabling condition to the enabling condition in which the user may rotate, slide, or otherwise move lock 130 of trigger mechanism 116 relative to housing 104 and the user may actuate expelling mechanism 106. For example, exemplary lock 130 may be configured to rotate approximately 10° relative to housing 4 when locking mechanism 120 is in the enabling condition.

When in the liquid phase, locking mechanism 120 remains positioned within the volume defined by recesses 124, 134 such that locking mechanism 120 remains generally stationary relative to housing 104 and expelling mechanism 106 when in the enabling condition. As such, locking mechanism 120 maintains a generally consistent shape when in the disabling and enabling condition, i.e., locking mechanism 120 generally maintains the shape of the volume between recesses 124, 134 when in the enabling and disabling conditions. When in the liquid phase, due to the presence of a gelling agent, the physical properties of the liquid locking mechanism 120 are such that it remains positioned with the volume defined by recesses 124, 134. Examples of gelling agents include, but are not limited to, pectin, hydrogels, methyl cellulose, or hydrophilic acrylate polymers.

Additionally, locking mechanism 120 provides a dampened force or resistance against the movement of lock 130 of trigger mechanism 116 relative to housing 104 such that locking mechanism 120 acts as a dampening grease or lubricant between housing 104 and expelling mechanism 106 when the user moves lock 130.

When button 128 is depressed, plunger 111 is triggered to move downwardly, thereby causing piston 110 to move downwardly to push a dosage of medication 114 through needle 112 and into the patient. As such, the user, not locking mechanism 120, applies the force required for triggering the administration of medication 114.

In one embodiment, medication delivery device 102 is configured for a single injection such that the complete dosage of medication 114 within syringe 108 is administered to the patient at one time. However, alternative embodiments of medication delivery device 102 may be configured for multiple uses such that multiple dosages of medication 114 are stored within syringe 108 and the user can use medication delivery device 102 to administer multiple dosages of medication 114 over a period of time.

For example, the user may administer a first dosage of medication 114 from medication delivery device 102 when locking mechanism 120 is the enabling condition and then subsequently store medication delivery device 102 at the low-temperature or refrigerated condition until it is desired to use medication delivery device 102 again. By decreasing the temperature of medication delivery device 102, including locking mechanism 120, after the first use, locking mechanism 120 transitions back to the solid phase and is stored in the disabling condition. More particularly, because locking mechanism 120 has substantially no hysteresis, locking mechanism 120 will transition from the enabling condition to the disabling condition when the temperature of locking mechanism 120 decreases to phase-change temperature A and remains in the disabling condition at temperatures below phase-change temperature A. As such, the user will be prevented from administering a second or subsequent dosage of medication 114 from medication delivery device 102 until the temperature of locking mechanism 120 has increased at least to phase-change temperature A again.

When the user desires to use medication delivery device 102 a subsequent time, medication delivery device 102 is removed from the low-temperature condition and the user waits until the temperature of locking mechanism 120 increases to at least phase-change temperature A. When the temperature of locking mechanism 120 is at or above phase-change temperature A, locking mechanism 120 is in the enabling condition which allows the user to rotate or move lock 130 and depress button 128. When button 128 is depressed for the second or any subsequent time after the first dosage is administered, another dosage of medication 114 is administered to the patient through needle 112. As such, medication delivery device 102 may be used to administer multiple dosages of medication 114 without requiring the user to acquire a new medication delivery device 102 for each dosage of medication 114. As discussed above, mechanical lock 130 can be rotated to an unlocked position when locking mechanism 120 is in the liquid phase to enable medication delivery device to deliver the medication. When used in a multiple dosage device, mechanical lock 130 is configured to automatically return to the locked position after each injection. When locking mechanism 120 returns to a solid phase, it will again block mechanical lock 130 from moving to the unlocked position until it changes back to its liquid phase.

Figure 9:
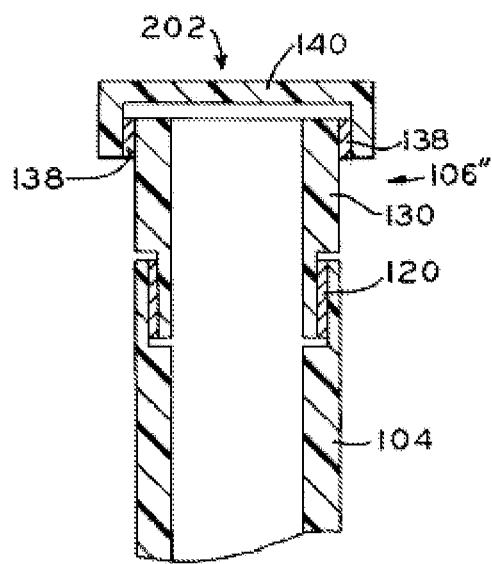
FIG. 9 is a schematic cross-sectional view of an alternative embodiment medication delivery device.
Figure 13:
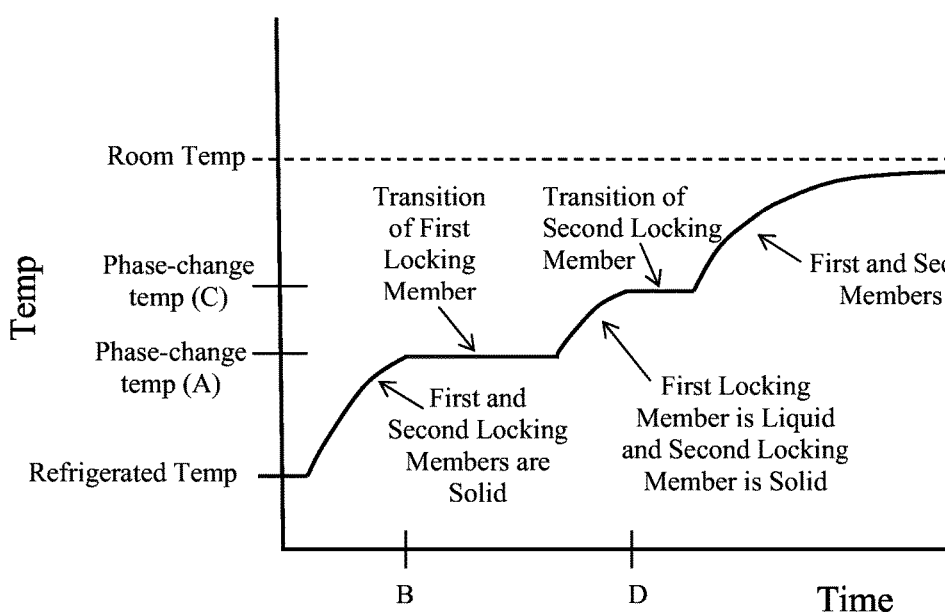
FIG. 13 is a graphical representation of the operation of a thermal locking mechanism of the alternative embodiment medication delivery devices of FIGS. 10 and 11.

Referring to FIG. 9, medication delivery device 202 may be configured to administer medication 114 only when the temperature of locking mechanism 120 is within an approximate range of temperatures. Illustratively, an alternative embodiment of medication delivery device 202 may include a second locking mechanism 138 and a cap 140. Button 128 (see FIG. 4, not shown in FIG. 9) may extend upwardly through cap 140. Cap 140 may be operably coupled to an upper end of expelling mechanism 106" and second locking mechanism 138 may be positioned therebetween. As shown in FIG. 13, second locking mechanism 138 has a second phase-change temperature C which is greater than phase-change temperature A of locking mechanism 120. For example, in one embodiment, second phase-change temperature C may be approximately 30° C. Second phase-change temperature C may correspond to a temperature of medication 114 at which it would be inefficient, unsuitable, inaccurate, and/or uncomfortable for the recipient. As such, second locking mechanism 138 is configured to remain in a solid phase until the temperature of second locking mechanism 138 increases to second phase-change temperature C. By remaining in the solid phase at a temperature above phase-change temperature A, but below second phase-change temperature C, cap 140 is prevented from moving relative to lock 130 of trigger mechanism 116 of expelling mechanism 106". More particularly, when in the solid phase, second locking mechanism 138 is a solid mass with high shear strength which prevents or blocks movement of cap 140 relative to lock 130, which allows the user to rotate lock 130. In this way, medication delivery device 202 remains enabled at a temperature at or above phase-change temperature A but below second phase-change temperature C because cap 140 rotates lock 130 when the user moves lock 130 to actuate medication delivery device 202.

However, if the temperature of second locking mechanism 138 increases to at least second phase-change temperature C, it may be uncomfortable, inefficient, unsuitable, and/or inaccurate to administer medication 14 to the patient. As such, if the temperature of second locking mechanism 138 increases to at least second phase-change temperature C, medication delivery device 202 will transition to a disabled condition to prevent the user from administering medication 114 at the elevated temperature. More particularly, if the temperature of second locking mechanism 138 increases to second phase-change temperature C, second locking mechanism 138 transitions from the solid phase to the liquid phase, thereby allowing cap 140 to rotate, slide, or otherwise move relative to lock 130 of expelling mechanism 106. As such, the user will only be able to move cap 140 at or above second phase-change temperature C but will not be able to rotate lock 130 to permit actuation of expelling mechanism 106". For example, illustrative cap 140 would be able to move relative to lock 130 of expelling mechanism 106" but lock 130 of expelling mechanism 106" would remain stationary and, therefore, the user would be unable to depress button 128. Only when the temperature of second locking mechanism 138 is a temperature at or less than second phase-change temperature C and the temperature of locking mechanism 120 is at or above phase-change temperature A is the user able to administer medication 114 from medication delivery device 202. In this way, the embodiment of medication delivery device 202 shown in FIG. 9 has an operating or enabled condition in which medication 114 may be administered only when locking mechanisms 120, 138 are within a range of operating temperatures (ex. at or between phase-change temperatures A and C).

Alternatively, medication delivery device 202 may include a second indicator (not shown) to indicate that the temperature of second locking mechanism 138, and therefore medication 114, is at an elevated temperature which is not desirable for injection.

According to another embodiment of the present disclosure, a medication delivery device can be disabled if it and/or its contents exceed a particular temperature (ex. 30° C.) for a period of time. According to this embodiment, a phase change material permits operation of the medication delivery device below the particular temperature, but disables the medication delivery device above the particular temperature device as discussed above. Similarly, in this embodiment the phase change material transmits force between components (ex. cap 140 and lock 130) when in a solid phase. However, when in a liquid phase, the phase change material flows or otherwise moves away from its initial location (i.e. when it was solid). When the phase change material returns to its solid phase, it is no longer positioned in its initial position between the components (ex. between cap 140 and lock 130) that permitted transfer of force between the components and the medical delivery device remains disabled. As such, the medical delivery device is irreversible because it cannot be enabled after the temperature drops below the particular temperature even though the phase-change material returned to its solid phase. According to one embodiment, an indicator, such as a label, is provided on the medical delivery device that changes color when the particular temperature is exceeded to notify the user that the medication is no longer suitable for use and/or the medication delivery device has been permanently disabled. Such an indicator would not change back to its original color even if its temperature drops below the particular temperature.

Referring back to FIGS. 1-8, in some circumstances, it may be possible for expelling mechanism 106 to move relative to housing 104 before locking mechanism 120 is completely at the liquid phase and before medication 114 has reached the predetermined temperature corresponding to when locking mechanism 120 is in the liquid phase. For example, locking mechanism 120 transitions between the solid phase and the liquid phase over a period of time and this transition may begin before the temperature of medication 114 has increased to the predetermined temperature. More particularly, while the locking mechanism 120 transitions between the solid phase and the liquid phase, the temperature of locking mechanism 120 does not increase because locking mechanism 120 absorbs thermal energy to effectuate this phase transition. As such, locking mechanism 120 may be partially liquid and partially solid before the temperature of medication 114 has increased to the preferred temperature for injection. This partial liquidity of locking mechanism 120 may allow the user to move lock 130 of trigger mechanism 116 and depress button 128 before locking mechanism 120 has fully transitioned to the liquid phase and the temperature of medication 114 has increased to the predetermined temperature for injection. As such, it may be less comfortable for the patient and/or it may be inaccurate or inefficient if medication 114 is administered before locking mechanism 120 has completely transitioned to the liquid phase and the temperature of medication 114 has increased to the predetermined value.

Figure 10:
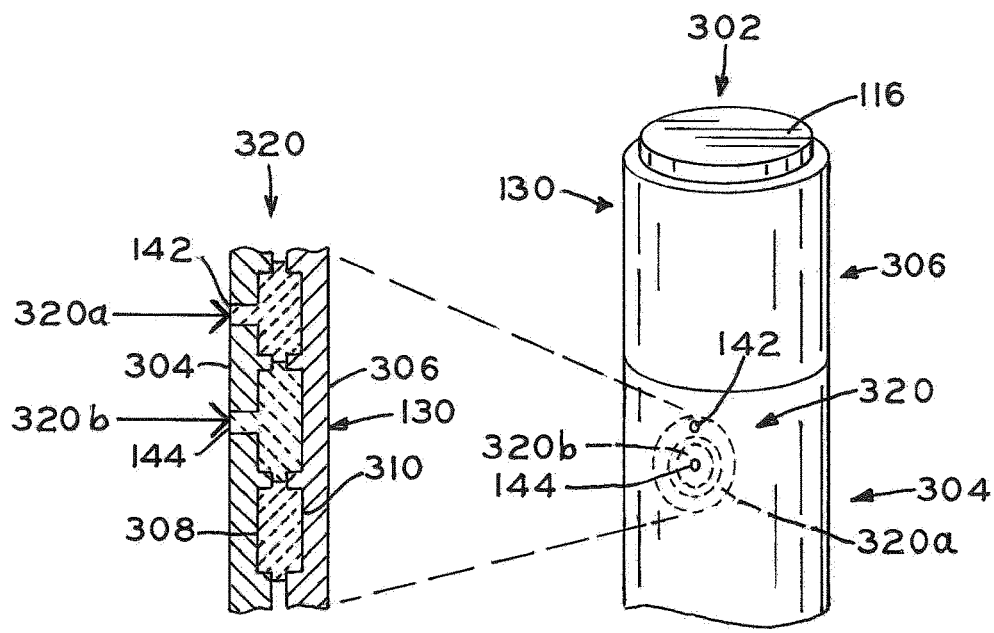
FIG. 10 is a schematic view of a further alternative embodiment medication delivery device.

However, as shown in FIG. 10, an alternative embodiment medication delivery device 302 is shown, which is provided with a secondary, supplemental, or buffer member to prevent premature actuation of medication delivery device 302. Medication delivery device 302 includes a housing 304 and an expelling mechanism 306. Housing 304 includes a first opening or aperture 142 and a second opening or aperture 144, as detailed further herein.

Expelling mechanism 306 includes trigger mechanism 116, a thermal locking mechanism 320, and delivery mechanism 118 (see FIGS. 2 and 3). Locking mechanism 320 includes a first member 320a and a second locking member 320b. Both first and second locking members 320a, 320b are illustratively supported intermediate an inner surface 308 of housing 304 and an outer surface 310 of lock 130 of expelling mechanism 306. As shown in FIG. 10, first member 320a generally surrounds second locking member 320b. First member 320a may be provided between housing 304 and expelling mechanism 306 through first opening 142, and second locking member 320b may be provided intermediate housing 304 and lock 130 of expelling mechanism 306 through second opening 144. In one embodiment, first and second locking members 320a and 320b are in a liquid phase when inserted through openings 142 and 144, respectively.

As shown in FIG. 13, first member 320a has a first phase-change temperature at which first member 320a is configured to transition between a solid phase and a liquid phase. For example, in one embodiment, first member 320a may have a phase-change temperature A of approximately 5-23° C. and, more particularly, of approximately 12-16° C. The exemplary embodiment of first member 320a may have a phase-change temperature A of approximately 15° C. In one embodiment, first member 320a is comprised of a paraffin wax material.

Second locking member 320b has a second phase-change temperature C at which second locking member 320b is configured to transition between a solid phase and a liquid phase. For example in one embodiment, second locking member 320b may have a phase-change temperature C of approximately 7-25° C. and, more particularly of approximately 14-20° C. The exemplary embodiment of second locking member 320b may have a phase-change temperature C of approximately 17° C. As such, second phase-change temperature C is greater than first phase-change temperature A. In one embodiment, second locking member 320b is comprised of a paraffin wax material.

Because phase-change temperature C of second locking member 320b may be greater than phase-change temperature A of first member 320a, first member 320a is configured to transition from the solid phase to the liquid phase at a temperature less than that of second locking member 320b. However, medication delivery device 302 is not configured to administer medication 114 until both first and second locking members 320a and 320b have transitioned from the solid phases to the liquid phases. As such, first member 320a is configured to "buffer" or otherwise delay the onset of the phase-change transition of second locking member 320b to maintain the rate of thermal increase of locking mechanism 320 at the same rate of thermal increase of medication 114. In this way, because first member 320a absorbs thermal energy without increasing its temperature during the transition between the solid phase to the liquid phase, the temperature of second locking member 320b will not increase during the phase change of first member 320a and the phase change of second locking member 320b will be delayed. As such, second locking member 320b will not transition to the liquid phase until first member 320a has completely transitioned to the liquid phase. Therefore, the time necessary to increase the temperature of medication 114 to the predetermined temperature for injection will substantially correspond to the time at which second locking member 320b transitions between the solid phase and the liquid phase, thereby preventing premature injection of medication 114.

Figure 11:
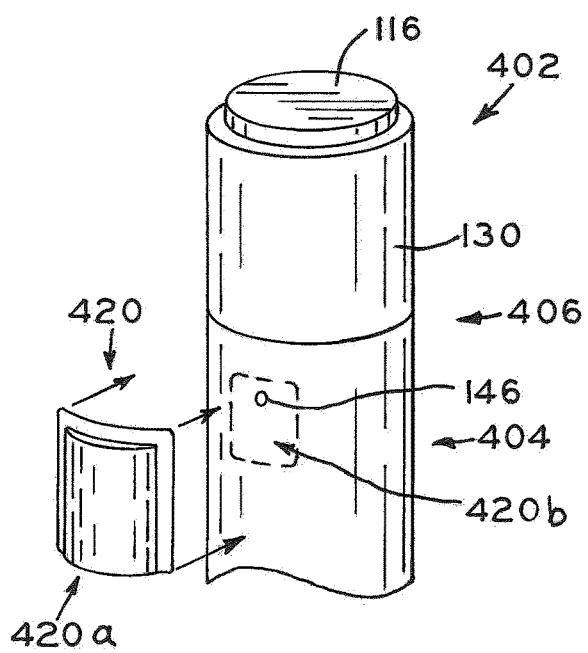
FIG. 11 is a schematic view of another alternative embodiment medication delivery device.

Similarly, as shown in FIG. 11, an alternative embodiment medication delivery device 402 is provided and also is configured to prevent premature injection of medication 114. Medication delivery device 402 includes a housing 404 and an expelling mechanism 406. Housing 404 includes an opening or aperture 146.

Expelling mechanism 406 includes trigger mechanism 116, a locking mechanism 420, and delivery mechanism 118. Locking mechanism 420 includes a first member 420a and a second locking member 420b. First member 420a is configured as a removable panel, label, cover, or other member comprised of a phase-change material. First member 420a is configured to be positioned over, or otherwise operably coupled to, second locking member 420b, which is supported on housing 404. More particularly, second locking member 420b may be positioned intermediate an inner surface (not shown; see, for example, inner surface 308 of housing 304) of housing 404 and an outer surface (not shown; see, for example, outer surface 310 of lock 130) of expelling mechanism 406. Second locking member 420b may be provided between housing 404 and lock 130 of expelling mechanism 406 through opening 146. In one embodiment, second locking member 420b is in a liquid phase when inserted through opening 146.

First member 420a has a first phase-change temperature A at which first member 420a is configured to transition between a solid phase and a liquid phase. For example, in one embodiment, first member 420a may have a phase-change temperature A of approximately 5-23° C. and, more particularly, of approximately 12-16° C. The exemplary embodiment of first member 420a may have a phase-change temperature A of approximately 15° C. In one embodiment, first member 420a is comprised of a paraffin wax material.

Second locking member 420b has a second phase-change temperature C at which second locking member 420b is configured to transition between a solid phase and a liquid phase. For example in one embodiment, second locking member 420b may have a phase-change temperature C of approximately 7-25° C. and, more particularly of approximately 14-20° C. The exemplary embodiment of second locking member 420b may have a phase-change temperature C of approximately 17° C. As such, second phase-change temperature C is greater than first phase-change temperature A. In one embodiment, second locking member 420b is comprised of a paraffin wax material.

Because phase-change temperature A of second locking member 420b is greater than phase-change temperature C of first member 420a, first member 420a is configured to transition from the solid phase to the liquid phase at a temperature less than that of second locking member 420b. However, medication delivery device 402 is not configured to administer medication 114 until both first and second locking members 420a, 420b have transitioned from the solid phases to the liquid phases. As such, first member 420a is configured to "buffer" or otherwise delay the onset of the phase-change transition of second locking member 420b to maintain the rate of thermal increase of locking mechanism 420 at the same rate of thermal increase of medication 114. In this way, because first member 420a absorbs thermal energy without increasing its temperature during the transition between the solid phase to the liquid phase, the temperature of second locking member 420b will not increase during the phase change of first member 420a and the phase change of second locking member 420b will be delayed. As such, second locking member 420b will not transition to the liquid phase until first member 420a has completely transitioned to the liquid phase. Therefore, the time necessary to increase the temperature of medication 114 to the predetermined temperature for injection will substantially correspond to the time at which second locking member 420b transitions between the solid phase and the liquid phase, thereby preventing a premature injection of medication 114.

Referring to FIG. 13, the phase-change temperature of second locking members 320b, 420b, denoted as C, is greater than the phase-change temperature of first members 320a, 420a, denoted as A. As such, first members 320a, 420a will transition between the solid phase and the liquid phase at a first time B, which occurs before second locking members 320b, 420b transition between the solid phase and the liquid phase at time D. In this way, locking mechanisms 320 and 420 are not in their enabling condition until time D, which substantially corresponds to the time at which medication 114 is at the predetermined temperature for injection.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practices in the art to which this invention pertains.

What is claimed is:

1. A medication delivery device including a housing; a needled syringe supported by the housing and having a plunger and a volume configured to contain a medication; and an expelling mechanism operably coupled to the plunger, the medication delivery device further including:
a thermal locking mechanism operably coupled to the expelling mechanism, the thermal locking mechanism comprising a phase-change material having a phase-change temperature, the phase-change material configured to transition between a solid and a liquid or gel-like state at the phase-change temperature, and the thermal locking mechanism having a disabling condition configured to inhibit delivery of the medication and an enabling condition configured to permit delivery of the medication, the thermal locking mechanism transitioning between the disabling and enabling conditions at the phase-change temperature, wherein the expelling mechanism includes a button configured to be enabled when the thermal locking mechanism transitions to the enabling condition at the phase-change temperature.

2. The medication delivery device of claim 1, wherein the thermal locking mechanism is stationary relative to the housing when changing between the disabling and enabling conditions.

3. The medication delivery device of claim 1, wherein the thermal locking mechanism has a consistent shape when changing between the disabling and enabling conditions.

4. The medication delivery device of claim 1, wherein the expelling mechanism comprises a lock movable relative to the housing and engageable with the button, wherein the expelling mechanism includes a first expelling component operably supported by the housing, the first expelling component comprising the button or the lock, and the thermal locking mechanism inhibits movement of the first expelling component relative to the housing in the disabling condition, and the thermal locking mechanism permits movement of the first expelling component relative to the housing in the enabling condition and dampens relative movement of the first expelling component relative to the housing.

5. The medication delivery device of claim 1, wherein the thermal locking mechanism is configured to change back from the enabling condition to the disabling condition at the phase-change temperature as the amount of thermal energy of the thermal locking mechanism decreases.

6. The medication delivery device of claim 1, further comprising a plurality of medication dosages positionable within the housing, the expelling mechanism being configured to dispense at least a first medication dosage and a second medication dosage, and the first medication dosage being dispensable when the thermal locking mechanism changes between the disabling condition and the enabling condition at a first time interval, and upon an transition of the thermal locking mechanism from the enabling condition to the disabling condition after the first time interval, the second medication dosage being dispensable when the thermal locking mechanism changes between the disabling condition and the enabling condition at a second time interval after the dispensing of the first medication dosage.

7. The medication delivery device of claim 1, wherein said phase-change material is a first phase-change material, and the thermal locking mechanism includes a second phase-change material, the second phase-change material has a second phase-change temperature and is configured to transition between a solid and a liquid or gel-like states at the second phase-change temperature, the phase-change temperature is less than the second phase-change temperature to buffer the onset of the second phase-change temperature.

8. The medication delivery device of claim 1, wherein at least one of the housing and the expelling mechanism includes a recess configured to receive the thermal locking mechanism.

9. The medication delivery device of claim 1, wherein the thermal locking mechanism transitions from the disabling condition to the enabling condition as the thermal energy of the thermal locking mechanism increases.

10. The medication delivery device of claim 9, further comprising a second thermal locking mechanism operably coupled to the expelling mechanism, wherein the second thermal locking mechanism has a second thermal locking phase-change temperature that is higher than the phase-change temperature of said thermal locking mechanism, and the second thermal locking mechanism has a disabling condition inhibiting delivery of the medication and an enabling condition permitting delivery of the medication, the second locking mechanism transitioning between the disabling and enabling conditions at the second thermal locking phase-change temperature.

11. The medication delivery device of claim 1, wherein the thermal locking mechanism transitions from the enabling condition to the disabling condition as the thermal energy of the thermal locking mechanism decreases.

12. A medication delivery device including: a housing; a needled syringe supported by the housing and having a plunger and a volume configured to contain a medication; an expelling mechanism operably coupled to the plunger; and a thermal locking mechanism supported by the housing, the thermal locking mechanism having a disabling condition inhibiting delivery of the medication and an enabling condition permitting delivery of the medication, and the locking mechanism having a solid phase when in the disabling condition and a liquid condition when in the enabling phase, wherein the thermal locking mechanism includes a first phase-change material and a second phase-change material, the first phase-change material has a first phase-change temperature and is configured to transition between solid and liquid phases at the first phase-change temperature, and the second phase-change material has a second phase-change temperature and is configured to transition between solid and liquid phases at the second phase-change temperature, the first phase-change temperature is less than the second phase-change temperature to buffer the onset of the second phase-change temperature.

13. The medication delivery device of claim 12, wherein the first phase-change temperature is approximately 5° C. to approximately 23° C.

14. The medication delivery device of claim 13, wherein the first phase-change temperature is approximately 12° C. to approximately 16° C.

15. The medication delivery device of claim 12, wherein the second phase-change temperature is approximately 7° C. to approximately 25° C.

16. The medication delivery device of claim 15, wherein the second phase-change temperature is approximately 14° C. to approximately 20° C.

17. The medication delivery device of claim 12, wherein the second phase-change material is generally surrounded by the first phase-change material.

18. A medication delivery device including: means for housing a medication; means for delivering the medication; means for triggering actuation of the delivering means; and a thermal locking mechanism supported by the housing means and operably coupled to at least one of the delivering means and the triggering means, the thermal locking mechanism having a phase-change temperature and being configured to change physical phases between a solid phase and a liquid or gel-like phase at the phase-change temperature, wherein the housing means includes a housing member, the trigger means includes a trigger member operably coupled to the housing member, and at least one of an inner surface of the housing member and an outer surface of the trigger member defines at least one recess, the at least one recess receives the thermal locking mechanism, and the thermal locking mechanism is configured to block relative movement of the housing member and the trigger member at a temperature below the phase-change temperature and permit relative movement of the housing member and the trigger member at a temperature at least as great as the phase-change temperature.

19. The medication delivery device of claim 18, wherein the housing member and the trigger member each define at least one recess.

20. The medication delivery device of claim 18, wherein the at least one recess includes a first recess defined by a portion of an inner surface of the housing member and a second recess defined by a portion of an outer surface of the trigger member.

21. The medication delivery device of claim 18, wherein the trigger means includes texture and the housing means includes texture, and each texture cooperates to create friction with the thermal locking mechanism.

* * * * *